United States Patent
Charrier et al.

(10) Patent No.: US 9,066,890 B2
(45) Date of Patent: *Jun. 30, 2015

(54) DYE COMPOSITION COMPRISING AN ALKOXYLATED FATTY ALCOHOL ETHER AND A FATTY ALCOHOL

(75) Inventors: Delphine Charrier, Boulogne Billancourt (FR); Evelyne Vacherand, Eaubonne (FR); Marie-Pascale Audousset, Asnieres (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/130,846

(22) PCT Filed: Jul. 5, 2012

(86) PCT No.: PCT/EP2012/063090
§ 371 (c)(1),
(2), (4) Date: Apr. 4, 2014

(87) PCT Pub. No.: WO2013/004772
PCT Pub. Date: Jan. 10, 2013

(65) Prior Publication Data
US 2014/0201931 A1   Jul. 24, 2014

Related U.S. Application Data

(60) Provisional application No. 61/523,908, filed on Aug. 16, 2011, provisional application No. 61/523,910, filed on Aug. 16, 2011.

(30) Foreign Application Priority Data

Jul. 5, 2011   (FR) ..................... 11 56058
Jul. 5, 2011   (FR) ..................... 11 56065

(51) Int. Cl.
*A61K 8/86*   (2006.01)
*A61Q 5/10*   (2006.01)
*A61K 8/34*   (2006.01)
*A61K 8/39*   (2006.01)
*A61K 8/37*   (2006.01)

(52) U.S. Cl.
CPC ... *A61K 8/86* (2013.01); *A61Q 5/10* (2013.01); *A61K 8/342* (2013.01); *A61K 8/39* (2013.01); *A61K 8/34* (2013.01); *A61K 8/37* (2013.01)

(58) Field of Classification Search
CPC ............. A61Q 5/10; A61K 8/22; A61K 8/31; A61K 8/33; A61K 8/37; A61K 8/39; A61K 8/604; A61K 8/882
USPC ............................................ 8/405, 406, 554
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,100,739 A | 8/1963 | Kaiser et al. |
| 3,206,462 A | 9/1965 | McCarty |
| 3,227,615 A | 1/1966 | Korden |
| 3,472,840 A | 10/1969 | Stone et al. |
| 3,524,842 A | 8/1970 | Grossmann et al. |
| 3,578,386 A | 5/1971 | Kalopissis et al. |
| 3,589,978 A | 6/1971 | Kamal et al. |
| 3,617,163 A | 11/1971 | Kalopissis et al. |
| 3,632,559 A | 1/1972 | Matter et al. |
| 3,665,036 A | 5/1972 | Kalopissis et al. |
| 3,817,698 A | 6/1974 | Kalopissis et al. |
| 3,867,456 A | 2/1975 | Kalopissis et al. |

(Continued)

FOREIGN PATENT DOCUMENTS

| | | |
|---|---|---|
| CA | 1069522 A1 | 1/1980 |
| DE | 2359399 A1 | 6/1975 |

(Continued)

OTHER PUBLICATIONS

STIC Search Report dated Aug. 12, 2014.*
International Search Report for PCT/EP2012/063090.
Todd, Charles et al., "Volatile Silicone Fluids for Cosmetic Formulations," Cosmetics and Toiletries, vol. 91, Jan. 1976, pp. 29-32.
Porter, M.R., "Handbook of Surfactants," published by Chapman and Hall, NY, 1991, pp. 116-178.
International Search Report for co-pending application PCT/EP2012/063097.
International Search Report for co-pending application PCT/EP2012/063154.

(Continued)

*Primary Examiner* — Eisa Elhilo
(74) *Attorney, Agent, or Firm* — The Marbury Law Group, PLLC

(57) ABSTRACT

The present invention relates to a composition for dyeing keratin fibers, comprising: at least one nonionic ether of a polyoxyalkylenated fatty alcohol of formula (i) R—(O-Alk)$_n$OR' (i), in which: —R denotes a linear or branched, saturated or unsaturated $C_{10}$-$C_{30}$ hydrocarbon-based radical, —R' denotes a linear or branched, saturated or unsaturated $C_{10}$-$C_{30}$ hydrocarbon-based radical, which may be substituted with a hydroxyl radical, —n is an integer between 1 and 100 inclusive, and —Alk represents a linear or branched, preferably linear, ($C_1$-$C_6$)alkylene group such as ethylene or propylene, preferably ethylene, —at least one fatty alcohol comprising at least 20 carbon atoms; —at least one chemical oxidizing agent. The present invention also relates to a process using this composition, and to a multi-compartment device that is suitable for implementing the invention.

33 Claims, No Drawings

(56) References Cited

U.S. PATENT DOCUMENTS

| | | |
|---|---|---|
| 3,869,454 A | 3/1975 | Lang et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,955,918 A | 5/1976 | Lang |
| 3,966,904 A | 6/1976 | Green et al. |
| 3,985,499 A | 10/1976 | Lang et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,013,787 A | 3/1977 | Varlerberghe et al. |
| 4,025,301 A | 5/1977 | Lang |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,151,162 A | 4/1979 | Lang et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| RE30,199 E | 1/1980 | Rose et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,226,784 A | 10/1980 | Kalopissis et al. |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,390,689 A | 6/1983 | Jacquet et al. |
| 4,422,853 A | 12/1983 | Jacquet et al. |
| 4,445,521 A | 5/1984 | Grollier et al. |
| 4,555,246 A | 11/1985 | Grollier et al. |
| 4,579,732 A | 4/1986 | Grollier et al. |
| 4,591,610 A | 5/1986 | Grollier |
| 4,608,250 A | 8/1986 | Jacquet et al. |
| 4,645,663 A | 2/1987 | Grollier |
| 4,702,906 A | 10/1987 | Jacquet et al. |
| 4,719,099 A | 1/1988 | Grollier et al. |
| 4,719,282 A | 1/1988 | Nadolsky et al. |
| 4,761,273 A | 8/1988 | Grollier et al. |
| 4,777,040 A | 10/1988 | Grollier et al. |
| 4,839,166 A | 6/1989 | Grollier et al. |
| 4,874,554 A | 10/1989 | Lange et al. |
| 4,886,517 A | 12/1989 | Bugaut et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,061,289 A | 10/1991 | Clausen et al. |
| 5,089,252 A | 2/1992 | Grollier et al. |
| 5,196,189 A | 3/1993 | Jacquet et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 5,879,413 A | 3/1999 | Pengilly et al. |
| 5,888,252 A | 3/1999 | Mockli |
| 5,919,273 A | 7/1999 | Rondeau et al. |
| 5,958,392 A | 9/1999 | Grollier et al. |
| 5,993,490 A | 11/1999 | Rondeau et al. |
| 6,045,591 A | 4/2000 | Deneulenaere |
| 6,099,592 A | 8/2000 | Vidal et al. |
| 6,136,042 A | 10/2000 | Maubru |
| 6,179,881 B1 | 1/2001 | Henrion et al. |
| 6,284,003 B1 | 9/2001 | Rose et al. |
| 6,338,741 B1 | 1/2002 | Vidal et al. |
| 6,436,151 B2 | 8/2002 | Cottard et al. |
| 6,451,069 B2 | 9/2002 | Matsunaga et al. |
| 6,492,502 B2 | 12/2002 | Henrion et al. |
| 6,645,258 B2 | 11/2003 | Vidal et al. |
| 6,695,887 B2 | 2/2004 | Cottard et al. |
| 6,730,789 B1 | 5/2004 | Birault et al. |
| 6,797,013 B1 | 9/2004 | Lang et al. |
| 6,863,883 B1 | 3/2005 | Tsujino et al. |
| 7,927,383 B2 | 4/2011 | Hercouet et al. |
| 8,088,173 B2 | 1/2012 | Debain et al. |
| 2001/0001332 A1 | 5/2001 | Henrion et al. |
| 2001/0023515 A1 | 9/2001 | Cottard et al. |
| 2001/0032368 A1* | 10/2001 | Bone et al. .............. 8/405 |
| 2001/0044975 A1 | 11/2001 | Matsunaga et al. |
| 2002/0010970 A1 | 1/2002 | Cottard et al. |
| 2002/0050013 A1 | 5/2002 | Vidal et al. |
| 2002/0165368 A1 | 11/2002 | Henrion et al. |
| 2002/0184717 A9 | 12/2002 | Cottard et al. |
| 2003/0019051 A9 | 1/2003 | Vidal et al. |
| 2004/0234471 A1 | 11/2004 | Corbella et al. |
| 2006/0248662 A1* | 11/2006 | Legrand .............. 8/405 |
| 2007/0101513 A1 | 5/2007 | Javet et al. |
| 2008/0216253 A1 | 9/2008 | Noecker et al. |
| 2009/0151089 A1 | 6/2009 | Audousset |
| 2010/0180389 A1* | 7/2010 | Hercouet et al. ........... 8/416 |
| 2011/0126363 A1 | 6/2011 | Debain et al. |

FOREIGN PATENT DOCUMENTS

| | | |
|---|---|---|
| DE | 2527638 | 5/1976 |
| DE | 2538363 A1 | 5/1976 |
| DE | 3843892 A1 | 6/1990 |
| DE | 4133957 A1 | 4/1993 |
| DE | 4137005 A1 | 5/1993 |
| DE | 4220388 A1 | 12/1993 |
| DE | 19543988 A1 | 5/1997 |
| DE | 10129034 A1 | 12/2002 |
| EP | 0080976 A1 | 6/1983 |
| EP | 0122324 A1 | 10/1984 |
| EP | 0337354 A1 | 10/1989 |
| EP | 0714954 A2 | 6/1996 |
| EP | 0770375 A1 | 5/1997 |
| EP | 0850636 A1 | 7/1998 |
| EP | 0850637 A1 | 7/1998 |
| EP | 0918053 A1 | 5/1999 |
| EP | 0920856 A1 | 6/1999 |
| EP | 1062940 A1 | 12/2000 |
| EP | 1106167 A2 | 6/2001 |
| EP | 1133975 A2 | 9/2001 |
| EP | 1133976 A2 | 9/2001 |
| EP | 2062615 A2 | 5/2009 |
| EP | 2198927 A2 | 6/2010 |
| FR | 1221122 A | 5/1960 |
| FR | 1492597 A | 8/1967 |
| FR | 1516943 A | 2/1968 |
| FR | 1540423 A | 8/1968 |
| FR | 1560664 A | 3/1969 |
| FR | 1567219 A | 5/1969 |
| FR | 1583363 A | 10/1969 |
| FR | 2077143 A | 10/1971 |
| FR | 2080759 A | 11/1971 |
| FR | 2162025 A1 | 7/1973 |
| FR | 2189006 A1 | 1/1974 |
| FR | 2190406 A2 | 2/1974 |
| FR | 2252840 A1 | 6/1975 |
| FR | 2270846 A1 | 12/1975 |
| FR | 2275462 A1 | 1/1976 |
| FR | 2280361 A2 | 2/1976 |
| FR | 2285851 A1 | 4/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |

(56) References Cited

FOREIGN PATENT DOCUMENTS

| | | |
|---|---|---|
| FR | 2393573 A1 | 1/1979 |
| FR | 2413907 A1 | 8/1979 |
| FR | 2470596 A1 | 6/1981 |
| FR | 2502949 A1 | 8/1981 |
| FR | 2505348 A1 | 11/1982 |
| FR | 2519863 A1 | 7/1983 |
| FR | 2542997 A1 | 9/1984 |
| FR | 2570946 A1 | 4/1986 |
| FR | 2598611 A1 | 11/1987 |
| FR | 2733749 A1 | 11/1996 |
| FR | 2757385 A1 | 6/1998 |
| FR | 2788433 A1 | 7/2000 |
| FR | 2801308 A1 | 5/2001 |
| FR | 2803196 A1 | 7/2001 |
| FR | 2803197 A1 | 7/2001 |
| FR | 2923711 A1 | 5/2009 |
| GB | 738585 | 10/1955 |
| GB | 1026978 A | 4/1966 |
| GB | 1153196 A | 5/1969 |
| GB | 1195386 A | 6/1970 |
| GB | 1331819 A | 9/1973 |
| GB | 1514466 A | 6/1978 |
| GB | 1546809 A | 5/1979 |
| JP | 02019576 | 1/1990 |
| JP | 5163124 | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 97/44004 A1 | 11/1997 |
| WO | 99/48465 A1 | 9/1999 |
| WO | 01/66646 A1 | 9/2001 |
| WO | 03/029359 A1 | 4/2003 |
| WO | 2005/074873 A1 | 8/2005 |
| WO | 2013/004773 A2 | 1/2013 |
| WO | 2013/004784 A2 | 1/2013 |

OTHER PUBLICATIONS

Non-Final Office Action dated Aug. 20, 2014, for co-pending U.S. Appl. No. 14/130,795, entitled "Dye Composition Using a Long-Chain Ether of an Alkoxylated Fatty Alcohol and a Cationic Polymer, Processes and Devices Using the Same," filed Apr. 4, 2014.

Non-Final Office Action dated Aug. 20, 2014, for co-pending U.S. Appl. No. 14/130,800, entitled "Cosmetic Composition Rich in Fatty Substances Comprising a Polyoxyalkylenated Fatty Alcohol Ether and a Direct Dye and/or an Oxidation Dye, The Dyeing Method and the Device," filed Apr. 4, 2014.

* cited by examiner

DYE COMPOSITION COMPRISING AN ALKOXYLATED FATTY ALCOHOL ETHER AND A FATTY ALCOHOL

CROSS REFERENCE TO RELATED APPLICATIONS

This is a national stage application of PCT/EP2012/063090, filed internationally on Jul. 5, 2012, which claims priority to U.S. Provisional Application Nos. 61/523,908 and 61/523,910, both filed on Aug. 16, 2011, as well as French Application Nos. FR 1156058 and FR 1156065, both filed on Jul. 5, 2011, all of which are incorporated herein by their entireties.

The present invention relates to a composition for dyeing keratin fibers, comprising at least one oxidation dye, at least one nonionic compound such as a long-chain ether of a polyoxyalkylenated fatty alcohol, at least one particular fatty alcohol and/or one particular fatty acid ester and at least one chemical oxidizing agent.

The present invention also relates to a dyeing process using this composition, and to a multi-compartment device that is suitable for using this composition.

Many people have sought for a long time to modify the color of their hair and in particular to mask their gray hair.

One of the dyeing methods is "permanent" or oxidation dyeing, which uses dye compositions containing oxidation dye precursors, generally known as oxidation bases. These oxidation bases are colorless or weakly colored compounds, which, when combined with oxidizing products, may give rise to colored compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds. The variety of molecules used as oxidation bases and couplers allows a wide range of colors to be obtained.

It is also possible to use direct dyes in order especially to afford tints on the coloration obtained. These direct dyes are colored and coloring molecules that have affinity for fibers. Examples that may be mentioned include benzenic, anthraquinone, nitropyridine, azo, xanthene, acridine, azine and triarylmethane direct dyes.

Permanent dyeing processes thus consist in using, with the dye composition, an aqueous composition comprising at least one oxidizing agent. This oxidizing agent has several roles. The first is to bring about condensation of the oxidation dyes (bases and couplers), enabling appearance of the color. The second is to degrade partially the melanin of the hair, which, depending on the nature of the oxidizing agent present, leads to more or less pronounced lightening of the fibers. The oxidizing agent used is generally hydrogen peroxide.

Thus, the compositions used in processes of this type must be able to be mixed easily, and the rheology of the resulting mixture must be such that it can be spread easily without running beyond the areas to be dyed once in place, and must do so throughout the entire treatment.

Moreover, the mixtures must result in uniform colorations between the end of the hairs and the root (they are also said to be sparingly selective), and must be chromatic and powerful.

European patent application EP 1 106 167 describes oxidation dye compositions comprising, besides colorants, a nonionic compound derived from a long-chain ether of a polyoxyethylenated fatty alcohol. These compositions represented an improvement over the existing compositions, not only in terms of viscosity and viscosity stability during the leave-on time on the hair, but also in terms of dyeing results.

However, there is an ongoing search for ever more efficient colorations in terms of results, especially improvement of the uptake of the coloration and better color uniformity. There is also an ongoing search for compositions with improved use qualities especially in terms of ease of distribution on the head of hair and of removal on rinsing.

One of the objects of the present invention is to propose compositions for dyeing human keratin fibers such as the hair that do not have the drawbacks of the existing compositions.

These aims and others are achieved by the present invention, one subject of which is thus a composition for dyeing keratin fibers, in particular human keratin fibers such as the hair, comprising:
  at least one oxidation dye;
  at least one nonionic ether of a polyoxyalkylenated fatty alcohol of formula (i)

$$R—(O\text{-Alk})_n—OR' \qquad (i),$$

in which:
  R denotes a linear or branched, saturated or unsaturated $C_{10}$-$C_{30}$ hydrocarbon-based radical,
  R' denotes a linear or branched, saturated or unsaturated $C_{10}$-$C_{30}$ hydrocarbon-based radical, which may be substituted with a hydroxyl radical, said hydroxyl preferably being beta to the ether function,
  n is an integer between 1 and 100 inclusive, and
  Alk represents a linear or branched, preferably linear, ($C_1$-$C_6$)alkylene group such as ethylene or propylene, preferably ethylene,
  at least one compound chosen from fatty alcohols comprising at least 20 carbon atoms and fatty acid esters, the said esters being solid at room temperature and atmospheric pressure, and mixtures thereof;
  at least one chemical oxidizing agent.

A subject of the invention is also a dyeing process using the abovementioned composition.

Finally, the invention relates to multi-compartment devices using the composition of the invention.

Thus, the use of the dye composition of the invention leads to powerful, homogeneous colorations. These compositions are distributed easily on the head of hair and are removed easily on rinsing.

Other characteristics and advantages of the invention will emerge more clearly on reading the description and the examples that follow.

In the text hereinbelow, unless otherwise indicated, the limits of a range of values are included in that range.

The human keratin fibers treated via the process according to the invention are preferably the hair.

For the purposes of the present invention, and unless otherwise indicated:
  the term "inclusive" for a range of concentrations means that the limits of that range are included in the defined range.
  The human keratin fibers treated via the process according to the invention are preferably the hair.
  The expression "at least one" followed by an ingredient is equivalent to the expression "one or more" ingredients.
  The term "direct emulsion" means a microscopically heterogeneous and macroscopically homogeneous mixture of two mutually immiscible liquid substances of oil-in-water (O/W) type. The emulsion is composed of an oily phase dispersed in an aqueous phase.
  For the purposes of the present invention, the term "emulsion" thus means true emulsions, which are to be distinguished from microemulsions, which are thermodynamically stable systems, unlike true emulsions. The size of the droplets of the dispersed phase of the emulsions of the invention is preferably between 10 nm and 100 µm and preferably between 200 nm and 50 µm. This is the mean diameter D(3.2), which may be measured especially using a laser granulometer. The direct emulsion may be prepared via standard emulsion preparation processes that are well known to those skilled in the art.

The term "oxidizing agent" or "chemical oxidizing agent" according to the invention means an oxidizing agent other than atmospheric oxygen.

Oxidation Dyes

The composition according to the invention comprises one or more oxidation dyes.

The oxidation dyes are generally chosen from one or more oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and addition salts thereof.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and addition salts thereof, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 3-hydroxymethylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and addition salts thereof.

Among the ortho-aminophenols that may be mentioned, for example, are 2-aminophenol, 2-amino-5-methylphenol, 2-amino-6-methylphenol and 5-acetamido-2-aminophenol, and addition salts thereof.

Among the pyridine oxidation bases that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine oxidation bases that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and addition salts thereof, and the tautomeric forms thereof, when a tautomeric equilibrium exists.

Among the pyrazole oxidation bases that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino- 3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and addition salts thereof. 4,5-Diamino-1-(β-methoxyethyl)pyrazole, and addition salts thereof, may also be used.

A 4,5-diaminopyrazole will preferably be used as pyrazole compound, and even more preferentially 4,5-diamino-1-(β-hydroxyethyl)pyrazole and/or an addition salt thereof.

The oxidation base(s) each advantageously represent from 0.0001% to 10% by weight relative to the total weight of the composition, and preferably from 0.005% to 5% by weight relative to the total weight of the composition.

The composition according to the invention may optionally comprise one or more couplers advantageously chosen from those conventionally used in the dyeing of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methyl benzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl-[3,2-c]-1,2,4-triazole and 6-methylpyrazolo[1,5-a]benzimidazole, addition salts thereof, and mixtures thereof.

The coupler(s), if they are present, each advantageously represent from 0.0001% to 10% by weight relative to the total weight of the composition, and preferably from 0.005% to 5% by weight relative to the total weight of the composition.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

Additional Dyes:

The composition of the invention may also comprise one or more additional dyes chosen from direct dyes.

The latter dyes are more particularly chosen from ionic or nonionic species, preferably cationic or nonionic species. These direct dyes may be synthetic or of natural origin.

Examples of suitable direct dyes that may be mentioned include azo dyes; methine dyes; carbonyl dyes; azine dyes; nitro (hetero)aryl dyes; tri(hetero)arylmethane dyes; porphyrin dyes; phthalocyanine dyes, and natural direct dyes, alone or as mixtures.

More particularly, the azo dyes comprise an —N═N— function in which the two nitrogen atoms are not simultaneously engaged in a ring. However, it is not excluded for one of the two nitrogen atoms of the sequence —N═N— to be engaged in a ring.

The dyes of the methine family are more particularly compounds comprising at least one sequence selected from >C═C< and —N═C< in which the two atoms are not simultaneously engaged in a ring. However, it is pointed out that one of the nitrogen or carbon atoms of the sequences may be engaged in a ring. More particularly, the dyes of this family are derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro (hetero)aromatic dyes are more particularly nitrobenzene or nitropyridine direct dyes.

As regards the dyes of porphyrin or phthalocyanine type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts, may also be used.

When they are present, the direct dye(s) more particularly represent(s) from 0.0001% to 10% by weight and preferably from 0.005% to 5% by weight of the total weight of the composition.

Nonionic Ether of a Polyoxyalkylenated Fatty Alcohol of Formula (i)

As indicated previously, the composition according to the invention comprises at least one nonionic ether of a polyoxyalkylenated fatty alcohol of formula (i) below:

in which:
R denotes a linear or branched, saturated or unsaturated $C_{10}$-$C_{30}$ hydrocarbon-based radical,
R' denotes a linear or branched, saturated or unsaturated $C_{10}$-$C_{30}$ hydrocarbon-based radical, which may be substituted with a hydroxyl radical, said hydroxyl preferably being beta to the ether function,
n is an integer between 1 and 100 inclusive, and
Alk represents a linear or branched, preferably linear, ($C_1$-$C_6$)alkylene group such as ethylene or propylene, preferably ethylene.

According to one particularly advantageous embodiment of the invention, the radical Alk of formula (i) represents a group —CH$_2$—CH$_2$—.

More particularly, the nonionic ether of a polyoxyalkylenated fatty alcohol of formula (i) is such that R and R', independently of each other, denote a linear or branched, preferably linear, saturated or unsaturated, preferably saturated, C$_{12}$-C$_{20}$ and preferably C$_{14}$-C$_{18}$ hydrocarbon-based radical; R' possibly being substituted with at least one hydroxyl radical, said hydroxyl radical preferably being beta to the ether function, and n denotes an integer greater than or equal to 20, for example ranging from 20 to 100 and preferably from 40 to 80.

Preferably, R and R' denote an alkyl radical.

According to a more preferred embodiment, the nonionic ether of a polyoxyalkylenated fatty alcohol of formula (i) is such that: R denotes a C$_{16}$-C$_{18}$ alkyl radical, which is preferably linear, and R' denotes a C$_{14}$ alkyl radical, which is preferably linear, substituted with an OH group, said hydroxyl radical preferably being beta to the ether function, and n is equal to 60.

Preferably, the nonionic ether of formula (i) has the following formula

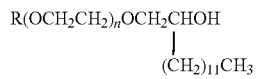

with R being a cetyl or stearyl group with n=60.

Such a compound is known, for example, in the CTFA dictionary under the name Ceteareth 60 myristyl glycol or Hydrogenated talloweth 60 myristyl glycol. A Ceteareth 60 myristyl glycol is sold, for example, by the company Akzo under the trade name Elfacos GT 282 S.

Preferably, the nonionic ether(s) of polyoxyalkylenated fatty alcohols (i) are present in a content ranging from 0.001% to 10% by weight and preferably from 0.001% to 5% by weight relative to the total weight of the composition.

The composition according to the invention comprises at least one compound chosen from fatty alcohols comprising at least 20 carbon atoms and fatty acid esters that are solid at room temperature and atmospheric pressure, and mixtures thereof.

This compound may be present in a content ranging from 0.01% to 20% by weight, preferably from 0.1% to 15% by weight and better still from 0.5% to 12% by weight relative to the total weight of the composition.

Fatty Alcohol Comprising at Least 20 Carbon Atoms:

The fatty alcohol(s) that are useful in the composition of the present invention are long-chain fatty alcohols comprising at least 20 carbon atoms, for example from 20 to 30 carbon atoms and better still from 20 to 24 carbon atoms. These fatty alcohols are neither oxyalkylenated nor glycerolated.

The fatty alcohols that are useful in the present invention comprise a hydrocarbon-based chain comprising at least 20 carbon atoms, which may be linear or branched, and saturated or unsaturated. Preferably, they are primary fatty alcohols with a saturated linear chain. Examples that may especially be mentioned include behenyl alcohol, arachidyl alcohol, lignoceryl alcohol, ceryl alcohol and montanyl alcohol, and mixtures thereof.

As mixture of fatty alcohols that is particularly preferred in the composition according to the invention, use may be made, for example, of the mixture of fatty alcohols formed from 76% by weight of behenyl alcohol, 17% by weight of arachidyl alcohol, 1.5% by weight of lignoceryl alcohol, 5% by weight of stearyl alcohol and 0.5% by weight of cetyl alcohol. This mixture is sold under the name Nafol® 1822 C by the company Condea. Other examples that may also be mentioned include the mixture sold under the name Nafol® 2298 by the company Condea, which comprises 98% by weight of behenyl alcohol; the mixture sold under the name Nafol® 20-22 by the company Condea, which comprises 30% by weight of behenyl alcohol, 58% by weight of arachidyl alcohol and 6% by weight of lignoceryl alcohol; or the mixture sold under the name Nafol® 20+ by the company Condea, which comprises 50% by weight of arachidyl alcohol, 29% by weight of behenyl alcohol, 14% by weight of lignoceryl alcohol and 6% by weight of stearyl alcohol.

The amount of the mixture of long-chain fatty alcohols comprising at least 20 carbon atoms in the composition according to the invention may preferably range from 0.1% to 20% by weight, preferably from 0.5% to 15% by weight and better still from 1% to 12% by weight relative to the total weight of the composition.

Solid Fatty Acid Ester:

The term "fatty acid ester that is solid at room temperature and atmospheric pressure" means a compound that is solid or pasty at 20 or at 25° C., with a reversible solid/liquid change of state, having a melting point of greater than about 40° C., which may be up to 200° C. It preferably has a hardness of greater than 0.5 MPa for solids and a hardness of between 0.001 and 0.5 MPa for pastes, and has at the melting point anisotropic crystal organization.

The fatty acid esters used in the present invention may be monoesters or polyesters, preferably monoesters, diesters or triesters.

They are preferably derived from the reaction:
of at least one carboxylic acid, preferably a monoacid, which is linear or branched, preferably linear, and saturated or unsaturated, preferably saturated, comprising from 10 to 50 carbon atoms, better still from 12 to 30 carbon atoms, preferably from 12 to 24 carbon atoms and in particular from 14 to 18 carbon atoms, and
of at least one alcohol chosen from a monoalcohol or a polyol, preferably a monoalcohol, which is linear or branched, preferably linear, and saturated or unsaturated, preferably saturated, advantageously comprising from 12 to 50 carbon atoms, better still from 12 to 24 carbon atoms and in particular from 14 to 18 carbon atoms.

Preferably, the solid fatty acid esters according to the invention are esters of a saturated linear monocarboxylic fatty acid comprising from 14 to 18 carbon atoms and of a saturated linear monoalcohol comprising from 14 to 18 carbon atoms.

Examples of solid fatty acid esters according to the invention that may be mentioned include cetyl myristate, stearyl myristate, myristyl myristate, palmityl palmitate, cetyl palmitate, stearyl palmitate, myristyl stearate, palmityl stearate and stearyl stearate, and mixtures thereof. Cetyl palmitate is used in particular.

The fatty acid ester(s) that are solid at room temperature and atmospheric pressure may be present in a content ranging from 0.01% to 15% by weight, preferably from 0.05% to 10% by weight and better still from 0.1% to 5% by weight relative to the total weight of the composition.

Fatty Substance:

The composition of the invention may optionally comprise, besides the fatty alcohol comprising at least 20 carbon atoms and/or the solid fatty ester, one or more "additional" fatty substances other than these particular fatty alcohols and solid fatty esters.

The term "fatty substance" means an organic compound that is insoluble in water at ordinary temperature (25° C.) and at atmospheric pressure (760 mmHg) (solubility of less than 5%, preferably 1% and even more preferentially 0.1%). They have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (COOH or COO⁻). Particularly, the fatty substances of the invention are neither polyoxyalkylenated nor polyglycerolated.

The term "oil" means a "fatty substance" that is liquid at room temperature (25° C.) and at atmospheric pressure (760 mmHg).

The term "nonsilicone oil" means an oil not containing any silicon atoms (Si) and the term "silicone oil" means an oil containing at least one silicon atom.

More particularly, the fatty substances are chosen from $C_6$-$C_{16}$ alkanes, nonsilicone oils of animal, plant, mineral or synthetic origin, fatty alcohols other than the fatty alcohols comprising at least 20 carbon atoms described above, esters of a fatty acid and/or of a fatty alcohol other than the solid fatty esters described above, nonsilicone waxes and silicones.

It is recalled that, for the purposes of the invention, fatty alcohols, esters and acids more particularly have at least one linear or branched, saturated or unsaturated hydrocarbon-based group comprising 6 to 30 carbon atoms, which is optionally substituted, in particular with one or more hydroxyl groups (in particular 1 to 4). If they are unsaturated, these compounds may have one to three conjugated or non-conjugated carbon-carbon double bonds.

As regards the $C_6$-$C_{16}$ alkanes, they are linear or branched, and possibly cyclic. Examples that may be mentioned include hexane, dodecane and isoparaffins such as isohexadecane and isodecane.

As oils of animal, plant, mineral or synthetic origin that may be used in the composition of the invention, examples that may be mentioned include:

hydrocarbon-based oils of animal origin, such as perhydrosqualene;
   triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.
   linear or branched hydrocarbons of mineral or synthetic origin, containing more than 16 carbon atoms, such as liquid paraffins, petroleum jelly, liquid petroleum jelly, polydecenes, and hydrogenated polyisobutene such as Parleam®;
   fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are non-oxyalkylenated and non-glycerolated. They are particularly of formula R—OH with R representing a linear or saturated $C_6$-$C_{19}$ alkyl group or a linear or branched $C_8$-$C_{18}$ alkenyl group. More particularly, the fatty alcohols are unsaturated or branched alcohols, comprising from 8 to 18 carbon atoms.

Examples that may be mentioned include cetyl alcohol, cetearyl alcohol and the mixture thereof (cetylstearyl alcohol), 2-butyloctanol, 2-hexyldecanol, oleyl alcohol and linoleyl alcohol.

As regards the esters of a fatty acid and/or of a fatty alcohol, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

Examples of esters or mixtures of esters of sugar and of fatty acid that may also be mentioned include:
  the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
  the products sold under the name Ryoto Sugar Esters, for example referenced B370 and corresponding to sucrose behenate formed from 20% monoester and 80% di-tri-ester-polyester;
  the sucrose mono-dipalmito-stearate sold by the company Goldschmidt under the name Tegosoft® PSE.

The nonsilicone wax(es) are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina); other waxes or waxy raw materials that may be used according to the invention are in particular marine waxes, such as that sold by Sophim under the reference M82, polyethylene waxes or polyolefin waxes in general.

The silicones that may be used in the cosmetic compositions of the present invention are volatile or nonvolatile, cyclic, linear or branched silicones, which are unmodified or modified with organic groups, having a viscosity from $5 \times 10^{-6}$ to $2.5$ m²/s at 25° C., and preferably $1 \times 10^{-5}$ to $1$ m²/s.

The silicones that may be used in accordance with the invention may be in the form of oils, waxes, resins or gums.

Preferably, the silicone is chosen from polydialkylsiloxanes, especially polydimethylsiloxanes (PDMS), and organomodified polysiloxanes comprising at least one functional group chosen from poly(oxyalkylene) groups, amino groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

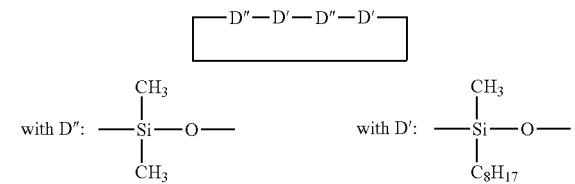

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Nonvolatile polydialkylsiloxanes, polydialkylsiloxane gums and resins, polyorganosiloxanes modified with organofunctional groups above, and mixtures thereof, are preferably used.

These silicones are more particularly chosen from polydialkylsiloxanes, among which mention may be made mainly of polydimethylsiloxanes containing trimethylsilyl end groups. The viscosity of the silicones is measured at 25° C. according to ASTM standard 445 Appendix C.

Among these polydialkylsiloxanes, mention may be made, in a nonlimiting manner, of the following commercial products:
  the Silbione® oils of the 47 and 70 047 series or the Mirasil® oils sold by Rhodia, for instance the oil 70 047 V 500 000;

the oils of the Mirasil® series sold by the company Rhodia; the oils of the 200 series from the company Dow Corning, such as DC200 with a viscosity of 60 000 mm²/s; the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly ($C_1$-$C_{20}$)dialkylsiloxanes.

The silicone gums that can be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:
  mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
  mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
  mixtures of two PDMSs with different viscosities, and more particularly of a PDMS gum and a PDMS oil, such as the product SF 1236 from the company General Electric. The product SF 1236 is a mixture of a gum SE 30 defined above with a viscosity of 20 m²/s and of an oil SF 96 with a viscosity of $5\times10^{-6}$ m²/s. This product preferably comprises 15% of gum SE 30 and 85% of an oil SF 96.

The organopolysiloxane resins that can be used in accordance with the invention are crosslinked siloxane systems containing the following units:

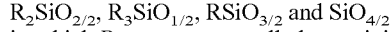

in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon-based group.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1\times10^{-5}$ to $5\times10^{-2}$ m²/s at 25° C.

Among these polyalkylarylsiloxanes, examples that may be mentioned include the products sold under the following names:
  the Silbione® oils of the 70 641 series from Rhodia;
  the oils of the series Rhodorsil® 70 633 and 763 from Rhodia;
  the oil Dow Corning 556 Cosmetic Grade Fluid from Dow Corning;
  the silicones of the PK series from Bayer, such as the product PK20;
  the silicones of the PN and PH series from Bayer, such as the products PN1000 and PH1000;
  certain oils of the SF series from General Electric, such as SF 1023, SF 1154, SF 1250 and SF 1265.

Among the organomodified silicones, mention may be made of polyorganosiloxanes comprising:
  polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;
  substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;
  alkoxy groups such as the product sold under the name Silicone Copolymer F-755 by SWS Silicones, and Abil Wax® 2428, 2434 and 2440 by the company Goldschmidt.

Preferably, the fatty substance(s) do not comprise any $C_2$-$C_3$ oxyalkylene units or any glycerolated units.

More particularly, the fatty substances are chosen from compounds that are liquid or pasty at room temperature (25° C.) and at atmospheric pressure.

Preferably, the fatty substance is a compound that is liquid at a temperature of 25° C. and at atmospheric pressure.

The fatty substance(s) are advantageously chosen from $C_6$-$C_{16}$ alkanes, nonsilicone oils of plant, mineral or synthetic origin, fatty alcohols comprising at least 20 carbon atoms, esters of a fatty acid and/or of a fatty alcohol, and silicones, or mixtures thereof.

Preferably, the fatty substance(s) are chosen from liquid petroleum jelly, $C_6$-$C_{16}$ alkanes, polydecenes, liquid esters of fatty acids and/or of fatty alcohols, and liquid fatty alcohols comprising at least 20 carbon atoms, or mixtures thereof.

Better still, the fatty substance(s) are chosen from liquid petroleum jelly, $C_6$-$C_{16}$ alkanes and polydecenes.

The composition according to the invention preferably comprises at least 25% by weight of fatty substance, preferably at least 30% by weight, better still at least 35% by weight and even better still at least 40% by weight of fatty substance.

The composition according to the invention more particularly has a fatty substance content ranging from 25% to 80% by weight, preferably from 30% to 70% by weight, even more advantageously from 40% to 70% by weight and more preferably from 40% to 60% by weight relative to the weight of the composition.

These amounts do not include the fatty alcohol(s) comprising at least 20 carbon atoms, nor the solid fatty acid ester(s) that is (are) solid at room temperature and atmospheric pressure.

Surfactants:

The composition of the invention may also comprise one or more "additional" surfactants other than the compounds (i).

In particular, the surfactant(s) are chosen from anionic, amphoteric, zwitterionic, cationic and nonionic surfactants, and preferentially nonionic surfactants.

The term "anionic surfactant" means a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH, =PO$^-$, the anionic parts comprising a cationic counterion such as an alkali metal, an alkaline-earth metal or an ammonium.

As examples of anionic surfactants that may be used in the composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, alpha-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and N-acyltaurates, salts of alkyl monoesters of polyglycoside-polycarboxylic acids, acyllactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids can be selected from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, the ammonium salts, the amine salts and in particular amino alcohol salts or the alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Among the anionic surfactants mentioned, use is preferably made of $(C_6$-$C_{24})$alkyl sulfates, $(C_6$-$C_{24})$alkyl ether sulfates comprising from 2 to 50 ethylene oxide units, especially in the form of alkali metal, ammonium, amino alcohol and alkaline-earth metal salts, or a mixture of these compounds.

It is particularly preferred to use $(C_{12}$-$C_{20})$alkyl sulfates, $(C_{12}$-$C_{20})$alkyl ether sulfates comprising from 2 to 20 ethylene oxide units, especially in the form of alkali metal, ammonium, amino alcohol and alkaline-earth metal salts, or a mixture of these compounds. Better still, use is made of sodium lauryl ether sulfate containing 2.2 mol of ethylene oxide.

The amphoteric or zwitterionic surfactant(s), which are preferably nonsilicone, which can be used in the present invention may especially be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of $(C_8$-$C_{20})$alkylbetaines, sulfobetaines, $(C_8$-$C_{20})$alkylamido$(C_3$-$C_8)$alkylbetaines and $(C_8$-$C_{20})$alkylamido$(C_6$-$C_8)$alkylsulfobetaines.

Among the optionally quaternized secondary or tertiary aliphatic amine derivatives that can be used, as defined above, mention may also be made of the compounds of respective structures (A1) and (A2):

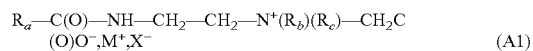

(A1)

in which formula (A1):

$R_a$ represents a $C_{10}$-$C_{30}$ alkyl or alkenyl group derived from an acid $R_a$—COOH preferably present in hydrolyzed coconut oil, or a heptyl, nonyl or undecyl group;

$R_b$ represents a beta-hydroxyethyl group; and $R_c$ represents a carboxymethyl group;

$M^+$ represents a cationic counterion derived from an alkali metal or alkaline-earth metal, such as sodium, an ammonium ion or an ion derived from an organic amine, and $X^-$ represents an organic or inorganic anionic counterion, such as that chosen from halides, acetates, phosphates, nitrates, $(C_1$-$C_4)$alkyl sulfates, $(C_1$-$C_4)$alkyl- or $(C_1$-$C_4)$alkylarylsulfonates, in particular methyl sulfate and ethyl sulfate; or alternatively $M^+$ and $X^-$ are absent;

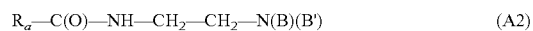

(A2)

in which formula (A2):

B represents the group —CH$_2$—CH$_2$—O—X';

B' represents the group —(CH$_2$)$_z$Y', with z=1 or 2;

X' represents the group —CH$_2$—C(O)OH, —CH$_2$—C(O)OZ', —CH$_2$—CH$_2$—C(O)OH, —CH$_2$—CH$_2$—C(O)OZ', or a hydrogen atom;

Y' represents the group —C(O)OH, —C(O)OZ', —CH$_2$—CH(OH)—SO$_3$H or the group —CH$_2$—CH(OH)—SO$_3$—Z';

Z' represents a cationic counterion derived from an alkali metal or alkaline-earth metal, such as sodium, an ammonium ion or an ion derived from an organic amine;

$R_a$' represents a $C_{10}$-$C_{30}$ alkyl or alkenyl group of an acid $R_a$'—C(O)OH preferably present in coconut oil or in hydrolyzed linseed oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caryloamphodiacetate, disodium cocoamphodipropionate, disodium lauroamphodipropionate, disodium caprylamphodipropionate, disodium caryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of $(C_8$-$C_{20})$alkylbetaines such as cocoylbetaine, and $(C_8$-$C_{20})$alkylamido$(C_3$-$C_8)$alkylbetaines such as cocamidopropylbetaine, and mixtures thereof. More preferably, the amphoteric or zwitterionic surface-active agent or agents are chosen from cocamidopropylbetaine and cocoylbetaine.

The cationic surfactant(s) that can be used in the compositions of the present invention comprise, for example, salts of optionally polyoxyalkylenated primary, secondary or tertiary fatty amines, quaternary ammonium salts, and mixtures thereof.

Examples of quaternary ammonium salts that may especially be mentioned include:

those corresponding to the general formula (A3) below:

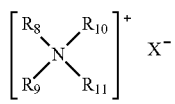

(A3)

in which formula (A3):

$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and $X^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkylacetate, $C_1$-$C_{30}$ hydroxyalkyl, $X^-$ is an anionic counterion chosen from halides, phosphates, acetates, lactates, ($C_1$-$C_4$)alkyl sulfates, and ($C_1$-$C_4$)alkyl- or ($C_1$-$C_4$) alkylarylsulfonates.

Among the quaternary ammonium salts of formula (A4), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A4) below:

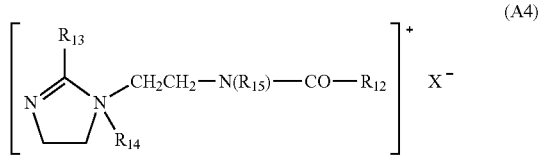

(A4)

in which formula (A4):

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an organic or inorganic anionic counterion, such as that chosen from halides, acetates, phosphates, acetates, lactates, ($C_1$-$C_4$)alkyl sulfates, ($C_1$-$C_4$)alkyl- or ($C_1$-$C_4$)alkylarylsulfonates.

$R_{12}$ and $R_{13}$ preferably denote a mixture of alkyl or alkenyl groups comprising from 12 to 21 carbon atoms, derived for example from tallow fatty acids, $R_{14}$ denotes a methyl group, and $R_{15}$ denotes a hydrogen atom. Such a product is sold, for example, under the name Rewoquat® W 75 by the company Rewo;

quaternary diammonium or triammonium salts, in particular of formula (A5) below:

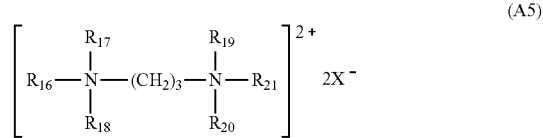

(A5)

in which formula (A5):

$R_{16}$ denotes an alkyl group comprising from about 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group —$(CH_2)_3$—$N^+$ $(R_{16a})(R_{17a})(R_{18a})$, $X^-$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$, which may be identical or different, represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts comprising one or more ester functional groups, such as those of formula (A6) below:

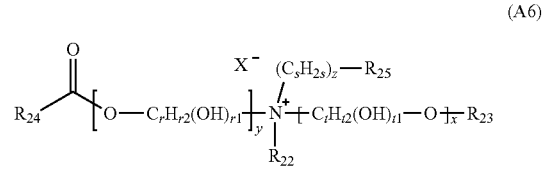

(A6)

in which formula (A6):

$R_{22}$ is chosen from $C_1$-$C_6$ alkyl and $C_1$-$C_6$ hydroxyalkyl or dihydroxyalkyl groups;

$R_{23}$ is chosen from:

the group

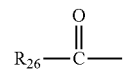

the groups $R_{27}$, which are linear or branched, saturated or unsaturated $C_1$-$C_{22}$ hydrocarbon-based radicals, a hydrogen atom, $R_{25}$ is chosen from:
the group

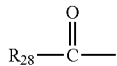

the groups $R_{29}$, which are linear or branched, saturated or unsaturated $C_1$-$C_6$ hydrocarbon-based radicals,
a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
r, s and t, which may be identical or different, are integers ranging from 2 to 6,
r1 and t1, which may be identical or different, are equal to 0 or 1, with r2+r1=2r and t1+t2=2t,
y is an integer ranging from 1 to 10,
x and z, which may be identical or different, are integers ranging from 0 to 10,
$X^-$ represents an organic or inorganic anionic counterion;
with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z has a value from 1 to 10.

When $R_{23}$ is a hydrocarbon-based group $R_{27}$, it may be long and may contain from 12 to 22 carbon atoms, or may be short and may contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which are identical or different, have values of 0 or 1.

Advantageously, y is equal to 1.

Preferably, r, s and t, which may be identical or different, are equal to 2 or 3, and even more particularly are equal to 2.

The anionic counterion $X^-$ is preferably a halide, such as chloride, bromide or iodide; a $(C_1$-$C_4)$alkyl sulfate or a $(C_1$-$C_4)$alkyl- or $(C_1$-$C_4)$alkylarylsulfonate. However, methanesulfonate, phosphate, nitrate, tosylate, an anion derived from an organic acid, such as acetate or lactate, or any other anion that is compatible with the ammonium containing an ester function, may be used.

The anionic counterion $X^-$ is even more particularly chloride, methyl sulfate or ethyl sulfate.

Use is made more particularly in the composition according to the invention of the ammonium salts of formula (A6) in which:
$R_{22}$ denotes a methyl or ethyl group,
x and y are equal to 1,
z is equal to 0 or 1,
r, s and t are equal to 2,
$R_{23}$ is chosen from:
the group

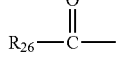

methyl, ethyl or $C_{14}$-$C_{22}$ hydrocarbon-based groups,
a hydrogen atom, $R_{25}$ is chosen from:
the group

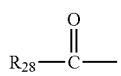

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and more particularly from linear or branched, saturated or unsaturated $C_{13}$-$C_{17}$ alkyl and alkenyl groups.

Advantageously, the hydrocarbon-based radicals are linear.

Among the compounds of formula (A6), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium salts of mono-, di- and triesters with a weight majority of diester salts.

It is also possible to use the ammonium salts containing at least one ester function that are described in patents U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Examples of additional nonionic surfactants that may be used in the composition used according to the invention are described, for example, in the "Handbook of Surfactants" by M. R. Porter, published by Blackie & Son (Glasgow and London), 1991, pp. 116-178. They are especially chosen from alcohols, alpha-diols and ($C_1$-$C_{20}$)alkylphenols, these compounds being polyethoxylated, polypropoxylated and/or polyglycerolated, and containing at least one fatty chain comprising, for example, from 8 to 18 carbon atoms, the number of ethylene oxide and/or propylene oxide groups possibly ranging especially from 2 to 50, and the number of glycerol groups possibly ranging especially from 2 to 30, said compounds being different than the compounds (i) of the invention.

Mention may also be made of copolymers of ethylene oxide and propylene oxide, optionally oxyethylenated fatty acid esters of sorbitan, fatty acid esters of sucrose, polyoxyalkylenated fatty acid esters, optionally oxyalkylenated alkylpolyglycosides, alkylglucoside esters, derivatives of N-alkylglucamine and of N-acylmethylglucamine, aldobionamides and amine oxides.

The additional nonionic surfactants are more particularly chosen from monooxyalkylenated or polyoxyalkylenated, monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include:
oxyalkylenated ($C_8$-$C_{24}$)alkylphenols;
saturated or unsaturated, linear or branched oxyalkylenated $C_8$-$C_{30}$ alcohols different than the compounds (i) of the invention;
saturated or unsaturated, linear or branched, oxyalkylenated $C_8$-$C_{30}$ amides;
esters of saturated or unsaturated, linear or branched $C_8$-$C_{30}$ acids and of polyethylene glycols;
polyoxyethylenated esters of saturated or unsaturated, linear or branched $C_8$-$C_{30}$ acids and of sorbitol;
saturated or unsaturated, oxyethylenated plant oils;
condensates of ethylene oxide and/or of propylene oxide, inter alia, alone or as mixtures;
oxyethylenated and/or oxypropylenated silicones.

The surfactants contain a number of moles of ethylene oxide and/or of propylene oxide of between 1 and 100, preferably between 2 and 50 and preferably between 2 and 30. Advantageously, the nonionic surfactants do not comprise any oxypropylene units.

In accordance with one preferred embodiment of the invention, the oxyalkylenated nonionic surfactants are chosen from saturated or unsaturated, linear or branched oxyalkylenated $C_8$-$C_{30}$ alcohols comprising between 1 and 100, preferably between 2 and 50 and even more particularly between 2 and 30 mol of ethylene oxide other than the compounds (i) of the invention; polyoxyethylenated esters of linear or branched, saturated or unsaturated $C_8$-$C_{30}$ acids and of sorbitol comprising from 1 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to formulae (A7) and (A'7) below:

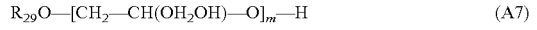

(A7)

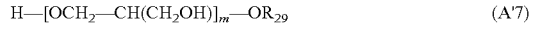

(A'7)

in which formulae (A7) and (A'7):
$R_{29}$ represents a linear or branched $C_8$-$C_{40}$ and preferably $C_8$-$C_{30}$ alkyl or alkenyl radical; and
m represents a number ranging from 1 to 30 and preferably from 1 to 10.

As examples of compounds of formula (A7) or (A'7) that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A7) or (A'7) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8$-$C_{10}$ alcohol containing 1 mol of glycerol, the $C_{10}$-$C_{12}$ alcohol containing 1 mol of glycerol and the $C_{12}$ alcohol containing 1.5 mol of glycerol.

Preferably, the additional surfactant(s) are chosen from nonionic surfactants other than the nonionic ethers of polyoxyalkylenated fatty alcohols of formula (i) or from anionic surfactants. More particularly, the surfactant(s) present in the composition are chosen from nonionic surfactants, other than the nonionic ethers of polyoxyalkylenated fatty alcohols of formula (i).

Preferably, the nonionic surfactant(s) are monooxyalkylenated or polyoxyalkylenated nonionic surfactants, particularly monooxyethylenated or polyoxyethylenated, or monooxypropylenated or polyoxypropylenated nonionic surfactants, or a combination thereof, more particularly monooxyethylenated or polyoxyethylenated nonionic surfactants, other than the nonionic ethers of polyoxyalkylenated fatty alcohols of formula (i).

Even more preferentially, the nonionic surfactants are chosen from polyoxyethylenated esters of sorbitol, oxyethylenated $C_8$-$C_{30}$ alcohols comprising from 1 to 100, preferably between 2 and 50 and even more particularly between 2 and 30 mol of ethylene oxide, other than the nonionic ethers of polyoxyalkylenated fatty alcohols of formula (i), and mixtures thereof. Even more preferentially, the nonionic surfactants are chosen from the abovementioned oxyethylenated $C_8$-$C_{30}$ alcohols.

Preferably, the additional surfactant used in the process of the invention in the composition is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated.

Even more preferentially, the nonionic surfactants are chosen from saturated or unsaturated, linear or branched polyoxyethylenated esters of $C_8$-$C_{30}$ acids and of sorbitol, saturated or unsaturated, linear or branched oxyalkylenated $C_8$-$C_{30}$ alcohols comprising between 1 and 100, preferably between 2 and 50 and preferably between 2 and 30 mol of ethylene oxide, other than the compounds (i) of the invention, and mixtures thereof.

In the composition of the invention, the amount of additional surfactant(s) in the composition preferably ranges from 0.1% to 50% by weight and better still from 0.5% to 20% by weight relative to the total weight of the composition.

The Basifying Agents:
The composition according to the invention may also comprise one or more basifying agents.

The basifying agent(s) may be mineral or organic or hybrid.

The mineral basifying agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chains comprising more than ten carbon atoms.

The organic basifying agent(s) are chosen, for example, from alkanolamines, oxyethylenated and/or oxypropylenated ethylenediamines, amino acids and the compounds of formula (I) below:

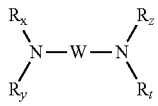
(I)

in which formula (I) W is a $C_1$-$C_6$ divalent alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl or $C_1$-$C_6$ hydroxyalkyl or $C_1$-$C_6$ aminoalkyl radical.

Examples of amines of formula (I) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (II) below, and also salts thereof:

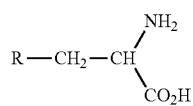
(II)

in which formula (II) R represents a group chosen from:

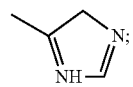

—$(CH_2)_3NH_2$;

—$(CH_2)_2NH_2$; —$(CH_2)_2NHCONH_2$; and

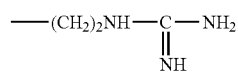

The compounds corresponding to formula (II) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the basifying agent(s) present in the composition of the invention are chosen from aqueous ammonia, alkanolamines, amino acids in neutral or ionic form, in particular basic amino acids, and preferably corresponding to those of formula (II).

Even more preferentially, the basifying agent(s) are chosen from aqueous ammonia and alkanolamines, most particularly monoethanolamine (MEA).

Better still, the basifying agent(s) are chosen from alkanolamines, most particularly monoethanolamine (MEA).

Advantageously, the composition according to the invention has a content of basifying agent(s) ranging from 0.01% to 30% by weight and preferably from 0.1% to 20% by weight relative to the weight of the composition.

Chemical Oxidizing Agent:

The composition of the invention also comprises one or more chemical oxidizing agents.

The term "chemical oxidizing agent" means an oxidizing agent other than atmospheric oxygen.

More particularly, the chemical oxidizing agent(s) are chosen from hydrogen peroxide, urea peroxide, alkali metal bromates, peroxygenated salts, for instance persulfates, perborates, peracids and precursors thereof and percarbonates of alkali metals or alkaline-earth metals.

This oxidizing agent is advantageously formed from hydrogen peroxide especially in aqueous solution (aqueous hydrogen peroxide solution), the concentration of which may range more particularly from 0.1% to 50% by weight, even more preferentially from 0.5% to 20% by weight and better still from 1% to 15% by weight relative to the weight of the composition.

Preferably, the composition of the invention does not contain any peroxygenated salts.

Solvent:

The composition according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The solvent(s), if they are present, represent a content usually ranging from 1% to 40% by weight and preferably from 5% to 30% by weight relative to the weight of the composition.

Other Additives:

The composition according to the invention may also contain various adjuvants conventionally used in hair dye compositions, such as anionic, cationic, nonionic, amphoteric or zwitterionic polymers or mixtures thereof; mineral thickeners, and in particular fillers such as organophilic silicas, fumed silicas, clays, especially organophilic clays, talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of composition.

The composition according to the invention preferably comprises at least one cationic polymer, more particularly chosen from substantive polymers such as alkyldiallylamine or dialkyldiallylammonium homopolymers (for instance Polyquaternium-6, Merquat 100, which is a dialkyldiallylammonium chloride homopolymer sold by the company Nalco), and also copolymers of these monomers and of acrylamide (for example copolymers of diallyldimethylammonium chloride and of acrylamide, sold especially under the name Merquat 550, Polyquaternium-7). Also suitable are the polymers of formula:

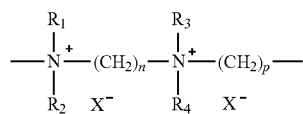

in which $R_1$, $R_2$, $R_3$ and $R_4$, which may be identical or different, denote a $C_1$-$C_4$ alkyl or hydroxyalkyl radical, n and p are integers ranging from 2 to 20 approximately, and $X^-$ is an anion derived from a mineral or organic acid.

According to one particular embodiment of the invention, use is made of polymers bearing repeating units of formulae (W) and (U) below:

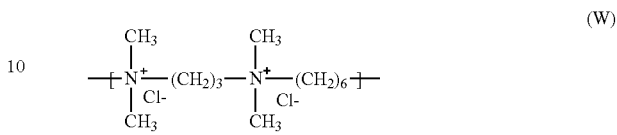

and especially those whose molecular weight, determined by gel permeation chromatography, is between 9500 and 9900;

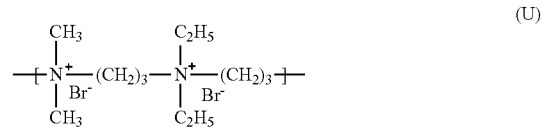

and especially those whose molecular weight, determined by gel permeation chromatography, is about 1200.

The concentration of cationic polymers in the composition, when they are present, ranges from 0.01% to 10% by weight relative to the weight of the composition, preferably from 0.1% to 5% by weight and better still from 0.2% to 3% by weight relative to the weight of the composition.

The composition may especially comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof.

Organophilic clays that may be mentioned include quaternium-18 bentonites such as those sold under the names Bentone 3, Bentone 38 and Bentone 38V by the company Rheox, Tixogel VP by the company United Catalyst, Claytone 34, Claytone 40 and Claytone XL by the company Southern Clay; stearalkonium bentonites such as those sold under the names Bentone 27 by the company Rheox, Tixogel LG by the company United Catalyst and Claytone AF and Claytone APA by the company Southern Clay; quaternium-18/benzalkonium bentonites such as those sold under the names Claytone HT and Claytone PS by the company Southern Clay.

The fumed silicas may be obtained by high-temperature pyrolysis of a volatile silicon compound in an oxhydric flame, producing a finely divided silica. This process makes it possible especially to obtain hydrophilic silicas having a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica via chemical reaction in order to reduce the number of silanol groups. It is especially possible to substitute silanol groups with hydrophobic groups: a hydrophobic silica is then obtained.

The hydrophobic groups may be:

trimethylsiloxyl groups, which are obtained especially by treating fumed silica in the presence of hexamethyldisilazane. Silicas thus treated are known as "silica silylate" according to the CTFA (6th Edition, 1995). They are sold, for example, under the references Aerosil R812® by the company Degussa and Cab-O-Sil TS-530® by the company Cabot.

dimethylsilyloxyl or polydimethylsiloxane groups, which are especially obtained by treating fumed silica in the presence of polydimethylsiloxane or dimethyldichlorosilane. Silicas thus treated are known as "silica dimethyl silylate" according to the CTFA (6th Edition, 1995). They are sold, for example, under the references Aerosil R972® and Aerosil R974® by the company Degussa, and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the mineral thickener represents from 1% to 30% by weight relative to the weight of the composition.

The composition may also comprise one or more organic thickeners.

These thickeners may be chosen from fatty acid amides (coconut diethanolamide or monoethanolamide, oxyethylenated carboxylic acid monoethanolamide alkyl ether), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum or scleroglucan gum), the crosslinked acrylic acid homopolymers whose INCI name is Carbomer, for instance the polymers sold by the company Lubrizol under the names Carbopol 980, 981 and Carbopol Ultrez 10, acrylate/$C_{10}$-$C_{30}$-alkylacrylate copolymers (INCI name: Acrylates/C10-30 Alkyl acrylate Crosspolymer) such as the products sold by the company Lubrizol under the trade names Pemulen TR1, Pemulen TR2, Carbopol 1382 and Carbopol EDT 2020, optionally crosslinked acrylamidopropanesulfonic acid homopolymers or copolymers, and associative polymers (polymers comprising hydrophilic regions and fatty-chain hydrophobic regions (alkyl or alkenyl comprising at least 10 carbon atoms), which are capable, in an aqueous medium, of reversibly combining with each other or with other molecules).

According to one particular embodiment, the organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum or scleroglucan gum) and crosslinked acrylic acid or acrylamidopropanesulfonic acid homopolymers, and preferably from cellulose-based thickeners in particular with hydroxyethylcellulose.

The content of additional organic thickener(s), if they are present, usually ranges from 0.01% to 20% by weight and preferably from 0.1% to 5% by weight relative to the weight of the composition.

The composition of the invention may be in various forms, for instance a solution, an emulsion (milk or cream) or a gel.

Processes of the Invention:

The composition described previously is applied to wet or dry keratin fibers.

It is usually left in place on the fibers for a time generally of from 1 minute to 1 hour and preferably from 5 minutes to 30 minutes.

The temperature during the dyeing process is conventionally between room temperature (between 15 and 25° C.) and 80° C. and preferably between room temperature and 60° C.

After the treatment, the human keratin fibers are advantageously rinsed with water. They may optionally be washed with a shampoo, followed by rinsing with water, and then dried or left to dry.

The composition applied in the process according to the invention is generally prepared extemporaneously before the application, by mixing at least two formulations, preferably two or three compositions and even more preferentially two formulations.

In particular, a formulation (A) free of chemical oxidizing agent and comprising at least one oxidation dye, at least one nonionic ether of a polyoxyalkylenated fatty alcohol of formula (i) and a formulation (B) comprising at least one chemical oxidizing agent are mixed together; at least one of the two formulations (A) and (B), preferably formulation (A), comprising at least one compound chosen from fatty alcohols comprising at least 20 carbon atoms and fatty acid esters that are solid at room temperature and atmospheric pressure, and mixtures thereof.

Advantageously, formulations (A) and (B) are aqueous.

The term "aqueous formulation" means a composition comprising at least 5% by weight of water, relative to the weight of this formulation.

Preferably, an aqueous formulation comprises more than 10% by weight of water and even more advantageously more than 20% by weight of water.

Preferably, formulation (A) comprises at least 50% by weight of additional fatty substance, other than the fatty alcohol comprising at least 20 carbon atoms and/or the solid fatty acid ester, and even more preferentially at least 50% by weight of fatty substances that are liquid at room temperature (25° C.), relative to the weight of this formulation (A).

Advantageously, formulation (A) is a direct emulsion (oil-in-water: O/W) or an inverse emulsion (water-in-oil: W/O), and preferably a direct emulsion (O/W).

More particularly, formulation (A) comprises at least one basifying agent.

In this variant, formulations (A) and (B) are preferably mixed together in a weight ratio (A)/(B) ranging from 0.2 to 10 and better still from 0.5 to 2.

According to one preferred embodiment, the composition used in the process according to the invention, i.e. the composition derived from mixing together the two compositions (A) and (B), preferentially has an additional fatty substance content of at least 25% by weight, relative to the weight of the composition derived from mixing together the two abovementioned formulations.

Everything that has been stated previously concerning the ingredients of the composition according to the invention remains valid in the case of the formulations (A) and (B), the contents taking into account the degree of dilution during mixing.

In a second variant of the invention, the composition used in the process according to the invention (thus in the presence of at least one chemical oxidizing agent) is derived from the mixing of three formulations. In particular, the three formulations are aqueous or alternatively at least one of them is anhydrous.

More particularly, for the purposes of the invention, the term "anhydrous cosmetic formulation" means a cosmetic formulation with a water content of less than 5% by weight, preferably less than 2% by weight and even more preferably less than 1% by weight relative to the weight of said composition. It should be noted that the water present in the composition is more particularly "bound water", such as water of crystallization in salts, or traces of water absorbed by the starting materials used in the preparation of the formulations according to the invention.

Preferably, use is made of two aqueous formulations (B') and (C') and an anhydrous formulation (A').

The anhydrous formulation (A') (free of chemical oxidizing agent) then preferably comprises at least one additional fatty substance, other than the fatty alcohol comprising at least 20 carbon atoms and/or the fatty acid ester that is solid at room temperature and atmospheric pressure, and more preferentially at least one fatty substance that is preferably liquid.

Formulation (B') (free of chemical oxidizing agent) then preferably comprises at least one oxidation dye and at least one nonionic ether of a polyoxyalkylenated fatty alcohol of formula (i).

Formulation (C') then preferably comprises at least one chemical oxidizing agent.

At least one of the three formulations (A'), (B') and (C') comprises at least one compound chosen from fatty alcohols comprising at least 20 carbon atoms and fatty acid esters that are solid at room temperature and atmospheric pressure, and mixtures thereof.

According to this preferred embodiment of the second variant, one or more basifying agents may be included in formulations (A') and/or (B') and preferably only in formulation (B').

As regards the surfactant(s) that may be present, they are preferably included in at least one of the formulations (A'), (B') and (C').

According to a preferred embodiment, the composition used in the process according to the invention, i.e. the composition derived from the mixing of the three formulations (A'), (B') and (C'), preferentially has an additional fatty substance content of at least 25% by weight, relative to the weight of the formulation derived from the mixing of the three above-mentioned formulations.

In this variant, formulations (A'), (B') and (C') are preferably mixed together in a weight ratio [(A')+(B')]/(C') ranging from 0.2 to 10 and more particularly from 0.5 to 2 and in a weight ratio (A')/(B') ranging from 0.5 to 10 and preferably from 1 to 5.

Everything that has been described previously regarding the ingredients of the composition according to the invention remains valid in the case of formulations (A'), (B') and (C'), the contents taking into account the degree of dilution during mixing.

Device:

Finally, the invention relates to a multi-compartment device that is suitable for implementing the composition and the process according to the invention, and comprising a first compartment containing formulation (A) as described above and a second compartment containing formulation (B) as described above.

The invention also relates to a second multi-compartment device comprising a first compartment containing formulation (A') as described above and a second compartment containing a cosmetic formulation (B') as described above and at least a third compartment comprising formulation (C') as described above.

The examples that follow serve to illustrate the invention without, however, being limiting in nature.

EXAMPLE

The following compositions are prepared (in which the amounts are expressed in grams of active materials):

Composition 1:

| | |
|---|---|
| Mineral oil (liquid paraffin) | 60 |
| Saturated C20-22 fatty alcohols (Nafol 2022 EN from Sasol) | 4.6 |
| Cetyl palmitate | 2 |
| Glycerol | 5 |
| Deceth-5 | 1.08 |
| Oleth-10 | 1 |
| Oleth-20 | 4 |
| Ceteareth-60 myristyl glycol (Elfacos GT 282 S from Akzo) | 0.01 |
| Carbomer (Carbopol 980 from Lubrizol) | 0.098 |
| 2,5-Tolylenediamine | 0.691 |
| m-Aminophenol | 0.11 |
| 2,4-Diaminophenoxyethanol, HCl | 0.018 |
| Resorcinol | 0.607 |
| Ethanolamine | 4.465 |
| 3,4-Dihydro-1,4-benzoxazin-6-ol | 0.03 |
| Sodium metabisulfite | 0.45 |
| Ascorbic acid | 0.25 |
| EDTA | 0.2 |
| Water | qs 100 |

Composition 2:

| | |
|---|---|
| Cetearyl alcohol | 6 |
| Mineral oil (liquid paraffin) | 20 |
| Glycerol | 0.5 |
| Hydrogen peroxide | 6 |
| Hexadimethrine chloride | 0.15 |
| Polyquaternium-6 (Merquat 100 from Nalco) | 0.2 |
| Oxyethylenated rapeseed acid amide (4 EO) | 1.2 |
| Steareth-20 | 5 |
| Tocopherol | 0.1 |
| Tetrasodium pyrophosphate | 0.03 |
| Sodium stannate | 0.04 |
| BHT | 0.001 |
| Pentasodium pentetate | 0.06 |
| Phosphoric acid | qs pH 2.2 |
| Water | qs 100 |

Application Method:

The two compositions are mixed together at the time of use in the following proportions:

10 g of composition 1
10 g of composition 2

The resulting mixture applies and is distributed easily onto a head of chestnut-brown hair containing gray hairs. It is left to stand on the hair for 30 minutes at room temperature. Removal with water is easy.

The hair is then washed with a standard shampoo and dried.

The hair coloration obtained is a uniform light chestnut with good coverage of the gray hairs.

The invention claimed is:

1. A composition for dyeing keratin fibers comprising:
   at least one oxidation dye;
   at least one nonionic ether of polyoxyalkylenated fatty alcohols of formula (i):

R—(OCH$_2$CH$_2$)$_n$—OR'  (i)

wherein:
   R denotes a linear or branched, saturated or unsaturated C$_{10}$-C$_{30}$ hydrocarbon-based radical,
   R' denotes a linear or branched, saturated or unsaturated C$_{10}$-C$_{30}$ hydrocarbon-based radical, optionally substituted with a hydroxyl radical, said hydroxyl radical optionally being beta to the ether function, and
   n is an integer ranging from 1 to 100, inclusive;
   at least one compound chosen from fatty alcohols comprising at least 20 carbon atoms, fatty acid esters that are solid at a temperature of about 25° C. and a pressure of about 760 mmHg, and mixtures thereof;

at least one chemical oxidizing agent; and
at least one additional fatty substance other than fatty alcohols comprising at least 20 carbon atoms and fatty esters that are solid at a temperature of about 25° C. and a pressure of about 760 mmHg, wherein said at least one additional fatt substance is chosen from liquid petroleum jelly, $C_6$-$C_{16}$ alkanes, polydecenes, liquid fatty alcohols comprising less than 20 carbon atoms, liquid esters of fatty acids or of fatty alcohols, and mixtures thereof, wherein the at least one compound is not chosen from oxyalkylenated fatty alcohols, and wherein the at least one additional fatty substance is present in an amount of at least about 25% by weight, relative to the total weight of the composition.

2. The composition according to claim 1, wherein:
the nonionic ether of polyoxyalkylenated fatty alcohols is chosen such that the radicals R and R', independently of each other, denote a linear or branched, saturated or unsaturated, $C_{12}$-$C_{20}$ hydrocarbon-based radical; R' optionally being substituted with at least one hydroxyl radical, and
n denotes an integer greater than or equal to 20.

3. The composition according to claim 1, wherein n denotes an integer ranging from 40 to 80, inclusive.

4. The composition according to claim 1, wherein the nonionic ether of polyoxyalkylenated fatty alcohols is chosen such that the radicals R and R' denote alkyl radicals.

5. The composition according to claim 1, wherein the nonionic ether of polyoxyalkylenated fatty alcohols is chosen such that R denotes a $C_{16}$-$C_{18}$ alkyl radical, and R' denotes a $C_{14}$ alkyl radical substituted with a group —OH, and n is equal to 60.

6. The composition according to claim 1, wherein R and R' are linear.

7. The composition according to claim 1, wherein the at least one nonionic ether of polyoxyalkylenated fatty alcohols (i) is present in an amount ranging from about 0.001% to about 10% by weight, relative to the total weight of the composition.

8. The composition according to claim 1, wherein the at least one nonionic ether of polyoxyalkylenated fatty alcohols (i) is present in an amount ranging from about 0.001% to about 5% by weight, relative to the total weight of the composition.

9. The composition according to claim 1, wherein the at least one compound chosen from fatty alcohols comprising at least 20 carbon atoms, fatty acid esters that are solid at a temperature of about 25° C. and a pressure of about 760 mmHg, and mixtures thereof, is present in an amount ranging from about 0.01% to about 20% by weight, relative to the total weight of the composition.

10. The composition according to claim 1, wherein the at least one compound chosen from fatty alcohols comprising at least 20 carbon atoms, fatty acid esters that are solid at a temperature of about 25° C. and a pressure of about 760 mmHg, and mixtures thereof, is present in an amount ranging from about 0.5% to about 12% by weight, relative to the total weight of the composition.

11. The composition according to claim 1, wherein the at least one compound chosen from fatty alcohols comprising at least 20 carbon atoms comprises from 20 to 30 carbon atoms.

12. The composition according to claim 1, wherein the at least one compound chosen from fatty alcohols comprising at least 20 carbon atoms comprises from 20 to 24 carbon atoms.

13. The composition according to claim 1, wherein the at least one compound chosen from fatty alcohols comprising at least 20 carbon atoms is chosen from saturated linear-chain fatty alcohols.

14. The composition according to claim 1, wherein the at least one compound chosen from fatty alcohols comprising at least 20 carbon atoms is chosen from behenyl alcohol, arachidyl alcohol, lignoceryl alcohol, ceryl alcohol, montanyl alcohol, and mixtures thereof.

15. The composition according to claim 1, wherein the at least one compound chosen from fatty alcohols comprising at least 20 carbon atoms is present in an amount ranging from about 0.1% to about 20% by weight, relative to the total weight of the composition.

16. The composition according to claim 1, wherein the at least one compound chosen from fatty alcohols comprising at least 20 carbon atoms is present in an amount ranging from about 1% to about 12% by weight, relative to the total weight of the composition.

17. The composition according to claim 1, wherein the fatty acid esters solid at a temperature of about 25° C. and a pressure of about 760 mmHg are derived from the reaction of:
at least one carboxylic acid, which is linear or branched, saturated or unsaturated, and comprises from 10 to 50 carbon atoms, and
at least one alcohol chosen from monoalcohols and polyols, which is linear or branched, saturated or unsaturated, and comprises from 12 to 50 carbon atoms.

18. The composition according to claim 17, wherein:
the at least one carboxylic acid is linear and saturated, and comprises from 14 to 18 carbon atoms, and
wherein the at least one alcohol is a linear, saturated monoalcohol comprising from 14 to 18 carbon atoms.

19. The composition according to claim 1, wherein the fatty acid esters solid at a temperature of about 25° C. and a pressure of about 760 mmHg are esters of a saturated linear monocarboxylic fatty acid comprising from 14 to 18 carbon atoms and a saturated linear monoalcohol comprising from 14 to 18 carbon atoms.

20. The composition according to claim 1, wherein the fatty acid esters solid at a temperature of about 25° C. and a pressure of about 760 mmHg are chosen from cetyl myristate, stearyl myristate, myristyl myristate, palmityl palmitate, cetyl palmitate, stearyl palmitate, myristyl stearate, palmityl stearate, stearyl stearate, and mixtures thereof.

21. The composition according claim 1, wherein the fatty acid esters solid at a temperature of about 25° C. and a pressure of about 760 mmHg are present in an amount ranging from about 0.01% to about 15% by weight, relative to the total weight of the composition.

22. The composition according to claim 1, wherein the fatty acid esters solid at a temperature of about 25° C. and a pressure of about 760 mmHg are present in an amount ranging from about 0.1% to about 5% by weight, relative to the total weight of the composition.

23. The composition according to claim 1, wherein the at least one additional fatty substance is present in an amount of at least about 40% by weight, relative to the total weight of the composition.

24. The composition according to claim 1, wherein the composition further comprises at least one basifying agent.

25. The composition according to claim 24, wherein the at least one basifying agent is chosen from aqueous ammonia, alkanolamines, and mixtures thereof.

26. The composition according to claim 1, wherein the composition further comprises at least one surfactant.

27. The composition according to claim 1, wherein the chemical oxidizing agent is hydrogen peroxide.

28. A method for dyeing keratin fibers, the method comprising applying to said fibers a composition comprising:
at least one oxidation dye;
at least one nonionic ether of polyoxyalkylenated fatty alcohols of formula (i):

R—(OCH$_2$CH$_2$)$_n$—OR'  (i)

wherein:
R denotes a linear or branched, saturated or unsaturated C$_{10}$-C$_{30}$ hydrocarbon-based radical,
R' denotes a linear or branched, saturated or unsaturated C$_{10}$-C$_{30}$ hydrocarbon-based radical, optionally substituted with a hydroxyl radical, said hydroxyl radical optionally being beta to the ether function, and
n is an integer ranging from 1 to 100, inclusive;
at least one compound chosen from fatty alcohols comprising at least 20 carbon atoms, fatty acid esters that are solid at a temperature of about 25° C. and a pressure of about 760 mmHg, and mixtures thereof;
at least one chemical oxidizing agent; and
at least one additional fatty substance other than fatty alcohols comprising at least 20 carbon atoms and fatty esters that are solid at a temperature of about 25° C. and a pressure of about 760 mmHg, wherein said at least one additional fatt substance is chosen from liquid petroleum jelly, C$_6$-C$_{16}$ alkanes, polydecenes, liquid fatty alcohols comprising less than 20 carbon atoms, liquid esters of fatty acids or of fatty alcohols, and mixtures thereof, wherein the at least one additional fatty substance is present in an amount of at least about 25% by weight, relative to the total weight of the composition.

29. The method according to claim 28, further comprising a step of preparing the composition extemporaneously before said application, by mixing at least two formulations comprising:
a formulation (A) free of chemical oxidizing agent and comprising at least one oxidation dye, at least one nonionic ether of polyoxyalkylenated fatty alcohols of formula (i); and
a formulation (B) comprising at least one chemical oxidizing agent;
wherein at least one of formulation (A) and formulation (B) comprises the at least one compound chosen from fatty alcohols comprising at least 20 carbon atoms, fatty acid esters that are solid at a temperature of about 25° C. and a pressure of about 760 mmHg, and mixtures thereof.

30. The method according to claim 29, wherein formulation (A) comprises formulation (A') and formulation (A"),
wherein formulation (A') is anhydrous, comprises at least one additional fatty substance other than fatty alcohols comprising at least 20 carbon atoms and fatty esters that are solid at a temperature of about 25° C. and a pressure of about 760 mmHg, and is free of chemical oxidizing agent;
wherein formulation (A") comprises at least one oxidation dye, at least one nonionic ether of a polyoxyalkylenated fatty alcohol of formula (i);
wherein at least one of formulation (A'), formulation (A"), and formulation (B) comprise at least one compound chosen from fatty alcohols comprising at least 20 carbon atoms, fatty acid esters that are solid at a temperature of about 25° C. and a pressure of about 760 mmHg, and mixtures thereof.

31. The method according to claim 29,
wherein at least one of formulation (A), formulation (A'), formulation (A"), and formulation (B), comprises the at least one additional fatty substance other than fatty alcohols comprising at least 20 carbon atoms and fatty esters that are solid at a temperature of about 25° C. and a pressure of about 760 mmHg.

32. A multi-compartment device for implementing a method for dyeing keratin fibers, the method comprising:
applying to said fibers a composition comprising:
at least one oxidation dye;
at least one nonionic ether of polyoxyalkylenated fatty alcohols of formula (i):

R—(OCH$_2$CH$_2$)$_n$—OR'  (i)

wherein:
R denotes a linear or branched, saturated or unsaturated C$_{10}$-C$_{30}$ hydrocarbon-based radical,
R' denotes a linear or branched, saturated or unsaturated C$_{10}$-C$_{30}$ hydrocarbon-based radical, optionally substituted with a hydroxyl radical, said hydroxyl radical optionally being beta to the ether function, and
n is an integer ranging from 1 to 100, inclusive;
at least one compound chosen from fatty alcohols comprising at least 20 carbon atoms, fatty acid esters that are solid at a temperature of about 25° C. and a pressure of about 760 mmHg, and mixtures thereof;
at least one chemical oxidizing agent; and
at least one additional fatty substance other than fatty alcohols comprising at least 20 carbon atoms and fatty esters that are solid at a temperature of about 25° C. and a pressure of about 760 mmHg, wherein said at least one additional fatt substance is chosen from h liquid petroleum jelly, C$_6$-C$_{16}$ alkanes, polydecenes, liquid fatty alcohols comprising less than 20 carbon atoms, liquid esters of fatty acids or of fatty alcohols, and mixtures thereof, wherein the at least one additional fatty substance is present in an amount of at least about 25% by weight, relative to the total weight of the composition;
preparing the composition extemporaneously before said application by mixing at least two formulations comprising:
a formulation (A) free of chemical oxidizing agent and comprising at least one oxidation dye and at least one nonionic ether of polyoxyalkylenated fatty alcohols of formula (i); and
a formulation (B) comprising at least one chemical oxidizing agent;
wherein at least one of formulation (A) and formulation (B) comprise the at least one compound chosen from fatty alcohols comprising at least 20 carbon atoms, fatty acid esters that are solid at a temperature of about 25° C. and a pressure of about 760 mmHg, and mixtures thereof;
the multi-compartment device comprising:
a first compartment for containing formulation (A), and
a second compartment for containing formulation (B).

33. The multi-compartment device according to claim 32,
wherein formulation (A) comprises formulation (A') and formulation (A"),
wherein formulation (A') is anhydrous, comprises the at least one additional fatty substance other than fatty alcohols comprising at least 20 carbon atoms and fatty esters that are solid at a temperature of about 25° C. and a pressure of about 760 mmHg, and is free of chemical oxidizing agent;

wherein formulation (A") comprises at least one oxidation dye, at least one nonionic ether of polyoxyalkylenated fatty alcohols of formula (i);

wherein at least one of formulation (A'), formulation (A"), and formulation (B) comprise at least one compound chosen from fatty alcohols comprising at least 20 carbon atoms, fatty acid esters that are solid at a temperature of about 25° C. and a pressure of about 760 mmHg, and mixtures thereof;

the first compartment of the multi-compartment device comprising a first sub-compartment for containing formulation (A') and a second sub-compartment for containing a formulation (A").

* * * * *

UNITED STATES PATENT AND TRADEMARK OFFICE
CERTIFICATE OF CORRECTION

| | | |
|---|---|---|
| PATENT NO. | : 9,066,890 B2 | Page 1 of 1 |
| APPLICATION NO. | : 14/130846 | |
| DATED | : June 30, 2015 | |
| INVENTOR(S) | : Delphine Charrier et al. | |

It is certified that error appears in the above-identified patent and that said Letters Patent is hereby corrected as shown below:

Claims

Claim 1, col. 31, line 6, change "fatt" to -- fatty --.

Claim 31, col. 34, line 34, change "fatt" to -- fatty -- and after "from" delete "h".

Signed and Sealed this
Tenth Day of November, 2015

Michelle K. Lee
*Director of the United States Patent and Trademark Office*